US006130309A

United States Patent [19]
Reich et al.

[11] Patent Number: 6,130,309
[45] Date of Patent: Oct. 10, 2000

[54] HYDROPHILIC POLYETHER POLYURETHANES CONTAINING CARBOXYLIC ACID

[75] Inventors: Murray H. Reich, Princeton; Ken Nelson, Lambertville, both of N.J.

[73] Assignee: Tyndale Plains-Hunter, Ltd., Lawrenceville, N.J.

[21] Appl. No.: 08/717,356

[22] Filed: Sep. 20, 1996

[51] Int. Cl.[7] ............ C08G 18/32; C08G 18/34; C08G 18/48; A61K 7/48
[52] U.S. Cl. .............. 528/76; 8/94.16; 424/63; 424/65; 424/70.1; 424/70.11; 424/401; 424/445; 521/157; 521/174; 521/176; 528/71; 528/904; 528/905; 602/41; 602/46; 604/304
[58] Field of Search ............... 528/71, 76, 904, 528/905; 8/94.16; 424/63, 65, 70.1, 70.11, 401, 445, 63.65; 602/41, 46; 604/304; 521/157, 174, 176

[56] References Cited

U.S. PATENT DOCUMENTS

| | | | |
|---|---|---|---|
| 3,412,054 | 11/1968 | Milligan et al. | 524/591 |
| 3,822,238 | 7/1974 | Blair et al. | 528/59 |
| 3,975,350 | 8/1976 | Hudgin et al. | 524/108 |
| 4,156,066 | 5/1979 | Gould | 528/73 |
| 4,156,067 | 5/1979 | Gould | 528/73 |
| 4,743,673 | 5/1988 | Johnston et al. | 528/60 |
| 5,120,816 | 6/1992 | Gould et al. | 528/76 |
| 5,281,654 | 1/1994 | Eisenhart et al. | 524/500 |
| 5,334,691 | 8/1994 | Gould et al. | 528/76 |
| 5,563,233 | 10/1996 | Reich et al. | 528/76 |
| 5,641,574 | 6/1997 | Kasari et al. | 428/413 |
| 5,643,581 | 7/1997 | Mougin et al. | 424/401 |

OTHER PUBLICATIONS

Sax et al.; *Hawley's Condensed Chemical Dictionary, Eleventh Edition*; Van Nostrand Reinhold; New York; 1987; p. 417.

*Primary Examiner*—Rabon Sergent
*Attorney, Agent, or Firm*—Mathews, Collins, Sherperd & Gould, P.A.

[57] ABSTRACT

An improved polyurethane is prepared by reacting a diol, an organic diisocyanate and a carboxylic acid with a critical selection of the amount of water in the reaction mixture. The polyurethane has improved adhesion, hydrophilicty and strength. The polymer has improved feel, and washability. Solutions of the polymer have low viscosity in aqueous solutions.

23 Claims, No Drawings

HYDROPHILIC POLYETHER POLYURETHANES CONTAINING CARBOXYLIC ACID

BACKGROUND OF THE INVENTION

1. Field of Invention

This invention relates to hydrophilic polyether polyurethanes having improved strength, good adhesion to different substrates, solubility in basic media, enhanced washability and which dissolve in neutral to slightly basic media to produce low viscosity solutions. The polymers are specifically adapted for use as adhesives, coatings, films, cosmetic applications, electroconductive surgical pads, shaving preparations, body and facial hair removal products, and antifogging agents.

2. Description of the Related Art

U.S. Pat. Nos. 3,822,238 and 3,975,350 describe a class of hydrophilic polyurethane polymers which on contact with an aqueous medium, absorb water with concomitant formation of a stable, water-insoluble hydrogel. In the water-swollen state, these polyurethanes vary from gel-like to soft and pliable and in the dry state from soft to hard and machinable.

U.S. Pat. Nos. 4,156,066 and 4,156,067 relate to a polyether polyurethane which contains a lactone group in the backbone and the polymer is subsequently swelled in a polar solvent such as acetone. The lactone group is ring opened with caustic to obtain a polymer with a carboxyl group in the polymer chain. These polymers have high solubility in neutral to base solutions, improved washability with ammonia and amines.

U.S. Pat. No. 4,743,673 describes a polymer containing an ester group which is neutralized in order to convert the sodium salts to carboxylic acid groups. This patent teaches that since carboxyl groups decarboxylate isocyanates, and since existing acidic diols were expensive, that the acid should to be shielded as an ester group. This process is complicated, lengthy and tedious. The polymer is made in two steps and the solvent must be added during the reaction in order to drive the reaction to completion. Then the polymer must be saponified, dissolved and the mixture is refluxed at the boiling temperature of the solvent for up to 11 hours, in order to make a water insoluble polymer which dissolves in water upon the addition of ammonia. The resulting polymer comprises a linear polyester diol.

U.S. Pat. No. 3,412,054 teaches the reaction of 4 to about 15% 2,2-di(hydroxymethyl) alkanoic acid with an isocyanate in order to produce polymers which become water soluble upon reaction with ammonia or an amine to form a quaternary salt. This patent teaches that the carboxyl group in alkanoic acidic diols does not react significantly with isocyanates to hinder the introduction of carboxylic acid groups into the polymer chain. The quaternary salts provide many hydrophilic sites which renders the urethane polymer water compatible if not water-soluble.

U.S. Pat. No. 5,120,816 relates to high strength hydrophilic polyether-polyester polyurethanes prepared at water levels in the reaction mixture of about 1.0 to 2.5%. This patent teaches that high tear strength polyether polyurethanes are achieved with less than 1% water. The hydrophilic polymers described in this patent are insoluble in water and polar solvents.

The above-described prior art introduces the carboxylic group into the polymer chain by lengthy and complicated processing steps and obtains a soluble polymer by neutralizing the acid with a base. It is desirable to provide polymers having higher strength and higher molecular weight and enhanced solubility in neutral to slightly basic media than lactone polymers and ester polymers.

SUMMARY OF THE INVENTION

It has now been found that the incorporation of a carboxylic acid containing diol into hydrophilic polyether polyurethanes produces polymers having excellent hydrophilicity, improved tear strength, enhanced washability, good adhesion, solubility in aqueous/polar solvents and form clear solutions in neutral to slightly basic aqueous solvents. In addition, solutions of hydrophilic polyurethanes made with the carboxylic acid containing diol in basic aqueous solvents produce clear sprayable solutions of low viscosity.

According to one embodiment of the present invention, hydrophilic polyurethanes are produced by reacting: (A) a diol component comprising a polyoxyalkylene diol; (B) an alkylene glycol; (c) a diisocyanate; (D) water in an amount constituting from about 0.002% to about 0.9% of the combined weight of the reactants; and (E) an 2,2-di(hydroxymethyl) alkanoic acid, preferably 2,2-di(hydroxymethyl) proprionic acid, in which the ratio of NCO to OH in the water, diol and glycol is from about 0.4 to about 1.1. The polymers are particularly useful as marine coatings, water absorptive gels, adhesives, anti-graffiti coatings, electroconductive surgical pads, and cosmetic applications such as shaving preparations, animal grooming products, and body and facial hair removal products.

The resulting polymer is a hydrophilic polyether polyurethane consisting of polyoxyalkylene units, so called soft segments and alkylene units, so-called hard segments connected through urethane linkages. Also interspersed in the polymer chain are small amounts of diol with appending carboxyl groups. The polymer chain also includes precise amounts of urea groups which originate from the reaction of water with isocyanate groups and modify the adhesive and hair styling properties of the polymer. It has been found that precisely controlling the combination of the different groups in specific proportions provides unique polymer properties such as hydrophilicity, high strength, superior adhesive and excellent properties for use in cosmetic applications.

In these polymers, polyoxyethylene soft segments impart hydrophilicity to the polymer. Soft hydrophobic units derived from polyoxypropylene and polyoxytetramethylene diols provide a softer more hydrophobic polymer for use in certain applications. Improved strength hydrophilic polymers with superior adhesive properties can be formed by using certain combinations of polyoxyalkylene diols for applications where tear strength and superior adhesion to substrates such as glass, skin, hair, and non-woven and woven cloth are used.

In another embodiment of the invention, in particular for cosmetic applications, the polymers are produced from (A) a major portion of polyoxyethylene diol having a molecular weight of 6000 to 10,000; (B) an alkylene glycol preferably diethylene glycol, cyclohexanedimethanol, and dipropylene glycol; (c) an aliphatic diisocyanate, (D) water in the amount comprising about 0.01% to about 0.8%; and (E) a 2,2-di(hydroxymethyl) alkanoic acid, the ratio of NCO to OH in the water, diol, and glycol mixture being about 0.40 to about 0.98. The polymers are specifically adapted for use in shaving preparations, body and facial hair removal products, and animal grooming products with the advantages of solubility in dilute (neutral to basic) aqueous solutions, sprayablity, and superior feel. In these applications, hydrophilicity is advantageous to provide breathabiliity and softness in a hydrated state.

In one aspect of the polymer produced with a major proportion of polyoxyethylene diol, water is added in the amount comprising about 0.02% to about 0.25%, and the ratio of NCO to OH of the water, diol and glycol mixture is from about 0.55 to about 0.98 to provide a polymer having improved slip, absorptivity, adhesiveness and biocompatibility.

The polymers are specifically adapted as adhesives to coat metal, skin, hair, glass and plastics for use in medical devices. The polymers are useful for forming gels in glycerine/water, water, and propylene glycol/water solutions and can be used in foams, cosmetic, animal grooming products, antiperspirants, and depilatories, gels, lotions and creams and shaving preparations.

DETAILED DESCRIPTION OF THE INVENTION

The present invention is based on the discovery that a class of hydrophilic polyether polyurethane polymers more fully described herein formed from the reaction product of a diol component, an aliphatic diisocyanate, water and a 2,2-di-(hydroxymethyl) alkanoic acid are advantageous in adhesives, cosmetic applications, depilatories, shaving preparations and coatings, coatings for catheters and guidewires, electroconductive surgical pads and gels. Alternatively, an amount of amine, such as diglycolamine can be used for at least a portion of the water in the reaction to form the reaction product. Solutions of the polymers for use in cosmetic applications have low viscosities in aqueous solvents. Also, for cosmetic and shaving applications, the polymers impart soft feel, breathability, slip, adhesion to skin and hair, and washability. In other applications, such as adhesives, the polymers have improved adhesion, hydrophilicity, and strength.

A first aspect of the present invention pertains to a hydrophilic polyether polyurethane comprising the reaction product of: a diol component comprising a polyoxyalkylene diol which can include polyoxyethylene diol having a molecular weight of from about 400 to about 20,000, polyoxypropylene diol having a number average molecular weight of about 200 to about 2500, block copolymers of ethylene oxide and propylene oxide having a molecular weight of about 1000 to about 9000 and polyoxytetramethylene diol having a number average molecular weight of about 200 to about 4,000; about 0.01% to about 10% of a low molecular weight alkylene glycol selected from ethylene glycol, propylene glycol, 2-ethyl-1-1,3-hexanediol, tripropylene glycol, triethylene glycol, 2,-4-pentane diol, 2-methyl-1,3-propanediol, 2,-methyl-1,3-pentanediol, cyclohexanediol, cyclohexanedimethanol, dipropylene glycol, diethylene glycol, and mixtures thereof, an organic diisocyanate, an 2,2-di-(hydroxymethyl) alkanoic acid, and water in an amount comprising from about 0.001% to about 0.95% of the reaction mixture, in which the NCO/OH ratio is from about 0.4 to about 1.1.

Alternatively, an amine can be used in the reaction for at least a portion of the water in the reaction mixture. The amine can be added to the reaction mixture in the range of about 0.01% to about 0.8% of the amine, preferably from about 0.02% to about 0.5% of the amine to about 0.01% to about 0.2% water in the reaction mixture. Preferably, the amine is diglycolamine. Amines which can be used in the reaction are ethylene diamine, propylene diamine, monoethanolamine, diglycolamine, propylene diamine, Jeffamine D1-230, D-400, D-2000, D-4000, ED-0600, ED-900, ED-2001. The hydroxylamines and the Jeffamines are manufactured by Texaco Chemical Company. Preferably, the amine used in the reaction is hydroxylamine, more preferably, the amine is monoethanolamine and digylcolamine, and most preferably the amine is diglycolamine. The polyoxyethylene diols are available from Union Carbide Corporation under the trademark and designation Carbowax, such as Carbowax® 8000 and Carbowax® 1450 wherein the numbers represent the number average molecular weight.

The polyoxypropylene diols are available from various sources such as from the PPG series of ARCO NIAX® PPG 1025, PPG-425, PPG-725, PPG 1225 and PPG 2025 and as R2134(2200) and R2135(4400) wherein the numbers represent the number average molecular weight. Triols are also available from ARCO as Niax polyols 11-34, LG-650, LG-56, LG-168, LHT-28, LHT-240.

The polyoxytetramethylene diols are available from E.I. DuPont de Nemours as Terathanes 600, 1000, 1400, 2000, 2900.

Polyetherpolycarbonate is available from BASF under the tradename polytetrahydrofuran 1000 CD and 2000 CD.

A block polyoxyalkylene diol polymer can also be used in the reaction. For example, a propylene oxide terminated block of ethylene glycol manufactured by BASF under the tradename Pluronic R and an ethylene oxide terminated block of propylene glycol manufactured by BASF under the tradename of Pluronic can be used for the polyoxyalkylene in the reaction mixture. Examples of the block copolymers of the sequential addition of ethylene oxide and propylene oxide to ethylene diamine are made by BASF under the tradename of Pluronics and Pluronics R such as F68, F64, F127, L35, L92, L82, 17R2 and 25R2.

Preferably, the blends of polyoxyalkylene diols contain at least about 10% of polyoxyethylene diol, more preferably, at least 20% of polyoxyethylene diol, and most preferably, at least about 25% of polyoxyethylene diol.

The amount of the polyoxyalkylene diol having a molecular weight of 400 to 20,000 in the polymer can vary from at least about 10%, preferably about 20%, more preferably about 30%, still more preferably about 35%, and most preferably about 40%, and the average molecular weight of the polyoxyalkylene diol can vary from about 400 to about 20,000, preferably 350 to 15,000, more preferably from about 400 to about 12,000, and still more preferably from about 400 to about 10,000.

The alkylene glycols can be purchased at chemical supply houses. For example, propylene glycol can be purchased from Aldrich Chemical Company as 1,2-propane diol. The amount of the alkylene glycol (hard segments), component can be from about 0.01% to about 20%, preferably from about 0.05% to about 15%, more preferably from about 0.1% to about 12%, still more preferably from about 0.5% to about 10%, and most preferably from about 1.0% to about 8% of the reaction mixture.

The diisocyanate used in the present invention can include both aliphatic and aromatic types and mixtures thereof although the aliphatics are preferred. An especially preferred isocyanate is methylene bis(cyclohexyl-4-isocyanate). Other examples of diisocyanates are trimethyl hexamethylene diisocyanate and isophorone diisocyanate. Representative examples of the preferred aliphatic diisocyanates include, but are not limited to tetramethylene diisocyanate, hexamethylene diisocyanate, trimethylene diisocyanate, trimethylene hexamethylene diisocyanate, cyclohexyl 1,2- diisocyanate, cyclohexylene 1,4-diisocyanate, and aromatic diisocyanates such as 2,4-toluene diisocyanates and 2,6-toluene diisocyanates. Also suitable are the isocyanate equivalents which form urethane linkages as exemplified by nitrile carbonates, such as adipontirile carbonate of the formulas (U.S. Pat. No. 4,810,543 of common ownership therewith). The amount of diisocyanate can vary from about 3% to about 80%, preferably from about 4% to about 70%, more preferably from about 5% to about 60%, still more preferably from about 6% to about 55%, and most preferably from about 6.5% to about 50%.

Preferably, the amount of water in the reaction mixture is in the range of from about 0.01% to about 0.75%, and more preferably from about 0.35% to about 0.55% of the reaction mixture.

The amount of 2,2-di-(hydroxymethyl) alkanoic acid in the reaction mixture is in the range from about 0.1% to about 30%, preferably from about 0.2% to about 20%, more preferably from about 0.3% to about 10%, still more preferably from about 0.4% to about 8%, and most preferably from about 0.5% to about 7.0%. Preferably the 2,2-di-(hydroxymethyl) alkanoic acid is dimethylolpropionic acid. The final reaction product has an acidic value of at least about 0.2, preferably at least about 0.5, more preferably at least about 0.8 and most preferably at least about 1.0.

The ratio of NCO to OH of the hydroxyl groups from the diol, alkylene glycol, amines, and water in the reaction mixture is preferably in the range from about 0.40 to about 1.0, and most preferably from about 0.50 to about 0.98. For this aspect of the invention, the most preferred ratio of NCO to OH is from about 0.9 to about 0.96. The most preferred weight average molecular weight of the polymer is from about 10,000 to about 500,000, preferably from about 40,000 to about 300,000. The sum of all ingredients, including the diols, glycols, water, and diisocyanate in the reaction mixture totals 100 parts by weight.

For this aspect, an aqueous solution containing a polar solvent, such as ethanol or tetrahydrofuran and water, can be formed with the concentration of polymer in the range of about 0.2% to about 40%, preferably about 0.5 to about 30%, more preferably from about 0.6 to about 25%, and most preferably from about 0.8 to about 20%. The solution is slightly basic having a pH of over about 7.0. The viscosity of the aqueous solution is less than about 3,000,000 cps, and preferably less than about 2,000,000 cps. In these solutions the polar solvents comprise at least about 5%, more preferably at least about 10%, still more preferably at least about 15%, most preferably at least about 20% of the solvent system.

Because of improved hydrophilicity, superior strength, and adhesion to certain substrates, the polymers find application as thickeners, in adhesives, coatings, wound dressings, cosmetic coatings, coatings of guidewires, catheters, Dacron cloth made under the trademark of Gortex for use in mechanical heart valves, synthetic veins and arteries for the peripheral and coronary system, and other surgical operations and coatings of other nonwoven materials such as polyethylene and polypropylene, boat coatings, electroconductive surgical pads, anti-graffiti coatings, coatings of metals, and adhesives. Also, films containing these polymers can be used as adhesives to metal, hair, glass, and skin with/without a commercial adhesive due to their superior adhesive and hydrophilic properties. The polymers also can reduce the elution rate of certain compounds from films such as appetite suppressants because they bond amino groups. Also, the polymer can irritate the skin and open the pores, permitting more drug to be introduced into the body. The acid containing polymers can be mixed with commercial adhesives such as those made by Monsanto Corporation under the trademark of Gelva adhesives to improve adhesion and moisture vapor transmission rates.

A second aspect of the present invention relates to a hydrophilic polyurethane adapted for cosmetic applications comprising the reaction product of a diol having a major portion of a polyoxyethylene diol having a number average molecular weight of 6,000 to 10,000, a minor portion of polyoxypropylene diol having a lower number average molecular weight of about 400 to about 3500, or polyoxyethylene diol having a number average molecular weight of about 600 to about 2000, an alkylene glycol, diisocyanate, water in an amount of about 0.01% to about 0.8% of the reaction mixture, a 2,2-di(hydroxymethyl)alkanoic acid in an equivalent mole weight ratio of NCO to OH of the water, diol and glycol of from about 0.50 to about 0.98. Preferably at least about 45% of polyoxyethylene diol of about 8000 number average molecular weight, more preferably at least about 55%, still more preferably at least about 65%, and most preferably at least about 75% of the polyoxyethylene diol of about 8000 number average molecular weight of the total reaction mixture is used and the amount of the lower molecular weight polyoxyethylene diol having a number average molecular weight of about 1,000 to about 3,500 is about 1% to about 15%, more preferably from about 2% to about 10% of the reaction mixture. Preferably, the alkylene glycol is diethylene glycol, cyclohexanedimethanol and dipropylene glycol.

The 2,2-di-(hydroxymethyl) alkanoic acid is preferably dimethylolpropionic acid. The amount of dimethylolpropionic acid is from about 0.1% to about 30%, preferably from about 0.2% to about 20%, more preferably from about 0.3% to about 10%, still more preferably from about 0.4% to about 8%, and most preferably from about 0.8 to about 6% of the reaction mixture. The final product has an acid value of at least about 0.2, preferably at least about 0.5, more preferably at least about 1.0.

Alternatively an amine equivalent can be used for the amount of water in the reaction mixture. An amount of about 0.15% to about 0.6% of amine, based on diglycolamine, is used with about 0.06% to about 0.5% of the water, more preferably of about 0.1% to about 0.40% of the water, and most preferably of about 0.15% to about 0.30% of the water.

The polymers of this aspect are specifically adapted for use in cosmetic applications such as shaving preparations and coatings, antiperspirants, animal grooming products, and facial and body hair removal products in which the polymers are soluble in ethanol/water mixtures and dilute neutral to basic aqueous solutions to form low viscosity solutions. The polymers also have the advantages in cosmetic applications of ease of forming improved gels in mixtures of hydrophilic and hydrophobic media, improved sprayablity of solutions, and of forming films with excellent breathability, high moisture and oxygen transmission rates, and soft feel.

For cosmetic applications, hydrophilicity is desirable in combination with other properties such as adhesion, feel, softness, breathability and washability. It has been found that the cosmetic properties are affected by small changes in the level of water, ratio of NCO/OH, and the level of the di(hydroxymethyl) alkanoic acid in the reaction mixture.

For cosmetic applications such as various hair removal, shaving preparations and coatings applications, the preferred diol is polyoxyethylene diol, preferably polyoxyethylene diol of about 6000 to about 10,000 number average molecular weight, alternatively with about 1.0% to about 10% of polyoxyethylene diol of about 1000 to 2000 number average molecular weight. The preferred water level is about 0.01% to about 0.65%, preferably from about 0.02% to about 0.60%, more preferably from about 0.05% to about 0.55%, and most preferably from about 0.10% to about 0.50%.

Further, it has unexpectedly been found that the weight average molecular weight of these polymers can be decreased or increased by up to about 20,000, by modifying the amount of water in the reaction mixture within a predetermined range. The above described polymers for cosmetic applications preferably have a weight average molecular weight of the reaction product of about 25,000 to about 55,000 and a kinematic viscosity at 3% in 55/42 ethanol/water of about 4.0 to about 40 centistokes (cts), formed from a range of water from about 0.10% to about 0.30% of the reaction mixture, a NCO/OH ratio of from about 0.75 to about 0.95, and a range of dimethylolpropionic acid of from about 0.5% to about 2.7% of the reaction mixture. A polymer having a weight average molecular weight of less than about 25,000 can be formed from a water level of from about 0.25% to about 0.40% of the reaction mixture, a ratio of NCO/OH from about 0.60 to about 0.75, and a range of dimethylolpropionic acid of from about 3.0% to about 6.5% of the reaction mixture. The polymer has a kinematic viscosity at 3% in a 55/42 ethanol water solution of about 1.0 to about 10 cts. This polymer is useful for forming low viscosity solutions in cosmetic product media. A polymer having a weight average molecular weight of about 55,000 to about 90,000 and a kinematic viscosity at 3% in 55/42 ethanol/water of about 10 to about 80 centistokes can be formed from a range of water from about 0.30% water to about 0.45%, a preferred range of the ratio of NCO/OH of from about 0.75 to about 0.98, and a range of dimethylolpropionic acid of from about 0.5% to about 2.7% of the reaction mixture. The polymer can form a gel in propylene glycol and water solution. The polymers are useful for adhesives, cosmetic applications such as shaving preparations, animal grooming products, depilatories, and antiperspirants, high slip coatings, drug delivery systems for its high absorptivity, as a thickener, and for pH sensitive applications. The polymer can be used in improved absorptive coatings and gels formed from the polymer in propylene glycol/water, water and glycerine/water solutions.

It has also been found that polymers of this aspect having an amount of water of about 0.08% to about 0.4% in the reaction mixture and a NCO/OH ratio of about 0.55 to about 0.95, preferably from about 0.60 to about 0.70 have low weight average molecular weights and form low viscosity solutions in water and ethanol/water mixtures that are useful in forming creams, lotions, and gels for use in cosmetic applications. An amount of water of about 0.15% to about 0.45% in the reaction mixture and a NCO/OH ratio is about 0.6 to about 0.92, preferably from about 0.70 to about 0.90 can be used for forming polymers having substantially high weight average molecular weights and form higher viscosity solutions in water and ethanol/water mixtures that are useful in forming creams, lotions, and gels for use in cosmetic applications. The films formed from these products have a soft feel, are tough, highly water absorptive, breathable and washable.

Alternatively, small amounts of diglycolamine may be substituted in place of the water in the reaction mixture, from about 0.02% to about 1.0%, preferably from about 0.03% to about 0.75%, more preferably from about 0.04% to about 0.5%, and most preferably from about 0.05% to about 0.4% of diglycolarine can be used in the reaction mixture.

The alkylene glycol used in this aspect can be selected from the group of ethylene glycol, diethylene glycol, propylene glycol, dipropylene glycol, cyclohexanediol, 1,4-butanediol, cyclohexanedimethanol, tripropylene glycol and triethylene glycol, preferably diethylene glycol, cycyclohexanedimethanol, and dipropylene glycol, more preferably diethylene glycol. The amount of the alkylene glycol (hard segments) is from about 0.01% to about 20%, preferably from about 0.05% to about 15%, more preferably from about 0.1% to about 12%, still more preferably from about 0.5% to about 10%, and most preferably from about 1.0% to about 5% of the reaction mixture.

For applications such as cosmetic applications including but not limited to antiperspirants, shaving preparations and coatings, and facial and body hair removal and animal grooming products, it is preferable that the kinematic viscosity of a solution of the polymer in a ratio of 55/42/3 of ethanol/water/polymer will be less than about 1,000 centistokes, preferably no more than about 500 cts, preferably no more than about 200, still more preferably less than about 100 cts, and most preferably less than about 80 cts.

In solutions of these polymers and in gels made with the polymers, the concentration of polymer in the solution is less than about 15%, preferably less than about 10%, more preferably less than about 8%, still more preferably less than about 7% by weight of the mixture. For use in shaving and cosmetic applications the solution can include at least about 5% water, preferably at least about 10% water, more preferably at least about 15% water, still more preferably at least about 30% water.

The polymers of the second aspect have pH sensitive properties. It has been found that a solution formed of about 5% of the polymer described in the second aspect in a 55% ethanol and 40% water solvent provides a milky solution having a viscosity of 12 cps. When the pH of the solution was neutralized with dilute ammonia, sodium hydroxide, triethanolamine, and other bases to a pH above about 7, the viscosity was 13 cps, and the solution unexpectedly became clear. In another example, the viscosity dropped from 1680 to 225 cps in a basic solution.

It has also been found that the hydrophilic carboxylic acid polyether polyurethanes formed in the second aspect of the invention form low viscosity solutions in aqueous polar solvents for use in cosmetic products, antiperspirants, shaving preparations, animal grooming, body and facial hair removal products, which possess excellent washability, adhesion to skin and hair, soft feel, and breathability, and which promote a healthy skin.

A third aspect of the present invention relates to hydrophilic polyether polyurethanes comprising the reaction product of a diol selected from a polyoxyalkylene diol selected from the group of polyoxyethylene diol having a number average molecular weight of about 4000 to about 15,000, a lower molecular weight polyoxypropylene diol having a number average molecular weight of about 400 to about 3,000 and a polyoxyethylene diol having a number average molecular weight of about 600 to about 2,000 and mixtures thereof, a 2,2-di(hydroxymethyl) alkanoic acid, diisocyanate, alkylene glycol, preferably ethylene glycol and dialkylene glycol, water in an amount of about 0.01% to about 0.80%, and an equivalent mole weight ratio of NCO/OH of from about 0.5 to about 0.98 for the water, diol and glycol.

The 2,2-di-(hydroxymethyl) alkanoic acid is preferably dimethylolpropionic acid. The amount of dimethylolpropionic acid is preferably from about 0.2% to about 20%, more preferably from about 0.35% to about 10%, still more preferably from about 0.4% to about 6%, and most preferably from about 0.5% to about 4%. The final product has an acid value of at least about 0.2, preferably at least about 0.5, more preferably at least about 0.8 and most preferably at least about 1.0.

Preferably, the amount of water in the reaction mixture is from about 0.01% to about 0.5%, more preferably from about 0.01% to about 0.4%, still more preferably from about 0.015% to about 0.3%, and most preferably from about 0.02% to about 0.25%. Alternatively an amine equivalent can be used for an amount of water in the reaction mixture. An amount of about 0.15% to about 0.6% of amine, based on diglycolamine, is used with about 0.02% to about 0.3% of the water.

For this aspect, the preferred diol is a high molecular weight polyoxyethylene diol having a number average molecular weight preferably of about 4000 to about 15,000, preferably from about 4500 to about 10,000, more preferably from about 6,000 to about 10,000 and the amount of the high molecular weight polyoxyethylene diol is at least about 50%, preferably at least about 60%, more preferably at least about 65%, still more preferably at least about 70%, and most preferably at least about 75% of the reaction mixture. Preferably, the NCO/OH ratio is from about 0.80 to about 0.99 and more preferably from about 0.84 to about 0.98.

The amount of diisocyanate in the reaction mixture for this aspect is from about 5% to about 60%, preferably from about 5% to about 40%, more preferably from about 7% to about 35%, and most preferably from about 8% to about 30%.

Alternatively, the amount of the lower molecular weight polyoxypropylene diol is from about 0.2% to about 20% of the reaction mixture, and preferably from about 1.0% to about 10% of the reaction mixture. The number average molecular weight of the polyoxypropylene diol is from about 400 to about 2200, and preferably from about 400 to about 1100. Alternatively, polyoxypropylene diol can be omitted from the reaction mixture.

Alternatively, a mixture of about 30% to about 80% of polyoxyethylene diol having an number average molecular weight of about 6,000 to about 10,000 and about 2% to about 30% of a polyoxyethylene diol having a number average molecular weight of about 1000 to about 3500 can be used in the reaction mixture at an NCO/OH ratio of about 0.80 to about 0.99 and an amount of water of about 0.01% to about 0.5%. Preferably the amount of water in the reaction mixture is from about 0.02% to about 0.3%. Preferably the NCO/OH ratio is from about 0.85 to about 0.98, and preferably the amount of the lower molecular weight polyoxyethylene diol is from about 3% to about 25%, and more preferably the amount of the lower molecular weight diol is from about 4% to about 20%, and more preferably the amount of the higher molecular weight diol is from about 40% to about 75% and more preferably the amount of water in the reaction mixture is from about 0.02% to about 0.25%.

It has unexpectedly been found that the viscosity of the above-described polymers in propylene glycol/water solutions and the weight average molecular weight of these polymers can be changed by adjusting the amount of water in the reaction formula and the NCO/OH ratio within narrow limits such as within about 0.10% of the water and within about 0.04 NCO/OH ratio, preferably within about 0.05% of the water and within about 0.02 NCO/OH ratio. A polymer having a weight average molecular weight of about 40,000 to about 200,000 and a kinematic viscosity at 3% in 55/42 ethanol/water of over 20 centistokes to insoluble can be formed from a preferred range of water from about 0.02% to about 0.30% of the reaction mixture, a preferred range of a ratio of NCO/OH from about 0.84 to about 0.98, and a preferred range of dimethylolpropionic acid of from about 0.5% to about 4.0% of the reaction mixture.

Gels, solutions, lotions, foams, and creams for shaving preparations, facial and body hair removal materials, depilatories and animal grooming products can be made with optional components that are well known to those skilled in the art. The optional components are emulsifiers such as anionic or nonionic surfactants; preservatives such as methyl paraben, propyl paraben, coloring agents, perfume oils, propellants for foams, waxes, vitamins, drugs, depilatory agents such as thioglycolic acid, foaming agents for shaving creams, and chelating agents such as ethylenediaminetetraacetic acid. The polymer is dissolved in an aqueous solution and the solution is cooled to about 50° to about 90° C. and the other ingredients are added. The preservatives are added at about 35° to 50° C.

For cream and lotion applications using polymers of this aspect comprising the combination of high and low molecular weight polyoxyethylene diols, the preferred level of the low molecular weight polyoxyethylene diol is from about 1% to about 25%, the preferred amount of water is about 0.02% to about 0.3% of the reaction mixture and the preferred NCO/OH ratio is from about 0.84 to about 0.98.

Because the polymers have high slip, good adhesion to metals, skin, plastics, and hair, and possess pH-sensitive viscosities, they are specifically adapted for use in coatings of Teflon and Dacron cloth, nonwoven polyethylene and polypropylene, guidewires, razors, silicon computer chips, catheters, plastics such as polyurethane, silicone rubber, polystyrene, polyolefins, wires for bone healing units, knives, metals, and pipe. The polymers can be incorporated into razor strips, and pre- and post-shaving preparations.

The polymers can be mixed with aqueous media to form gels for burn and wound care dressings and delivery of drugs by iontophoresis. The polymers can be used in foams for shaving preparations and other cosmetic applications. The polymers form gels in water, glycerine/water and propylene glycol/water media. The gels are tough, hydrophilic, possess enhanced washability, superior water absorptivity and adhesiveness to metals, glass, skin, hair, plastics and pH-sensitive viscosities. The gels are made by adding the polymer to water, water/glycerine and water/propylene glycol mixtures, stirring the mixture in a heated vessel or on a roller mill, and then mixing for about one hour at about 25° 80 to 95 C. The procedure is repeated until a homogeneous gel is obtained. Alternatively, mixtures of water, glycerine, polymer, and propylene glycol can be added to a heated vessel with an agitator and slowly heated and mixed to obtain uniform gels.

The polymers form films with excellent breathability, high moisture and oxygen transmission rates, and superior feel. The films may be formed by extruding the polymer through a film die, and by solvent casting. The polymer is dissolved in suitable solvents such as tetrahydrofuran, ethanol, water, propylene glycol, the solution is poured over a suitable flat surface, and the solvent is allowed to evaporate.

The improved adhesion and superior water absorptivity of the tough gels lend them to wound dressings, gels to hold devices, delivery of drugs. The high slip, water absorptivity and high moisture vapor transmission rate of the polymers enhance their use in skin lotions, thickeners, breathable films, nail polish, face make-up, antiperspirants, and shaving preparations such as stable and quick breaking foams, lotions, and creams. The increased hydrophilicity and superior slip of the polymers enhance their use as high slip coatings. The hydrophilic gels can be used as flowable viscous gels which can be squeezed out of tubes to provide a moist healing environment for wounds. The gels are especially useful, because the acidic gels provide an improved healing environment and also being pH sensitive, can be readily removed with a slightly neutral rinse. Also, the acid-containing polymers may absorb certain additives that are not readily adsorbed by non-acid containing polymers. The gels can be used to fill wound or holes in an emergency, and then to wash them out with a slightly basic rinse. The gels may be used for the delivery of drugs, because of their high absorptivity and for improved adhesion, and also, the gels, due to their acidity, may absorb different types of drugs. Also, improved adhesive gels can improve the contact of the gel with the skin, extremely important in iontophoresis and trans- dermal delivery of drugs. The polymers, coated onto nonwoven materials can absorb and release different types of drugs due to their high absorptivity and acidity.

For gels used for wound dressings, drug delivery systems, supports, and retainers for devices, the concentration of polymer in the media is preferably from about 5% to about 30%, more preferably from about 8% to about 25%, and most preferably from about 10% to about 22%. For applications such as gels, foams, amorphous gels, use in high slip and high absorptive coatings in which the viscosity of the media is sensitive to pH, and for pre- and post-shave preparations, facial and body hair removal products, face make-up and skin lotions, the concentration of polymer in the media is preferably from about 0.01% to about 10%, preferably from about 0.02% to about 8%, and most preferably from about 0.03% to about 6%.

The adhesive qualities of the gels are advantageous for shaving applications and hair removal products, because of the improved ability to stick to the hair. And the washability, high moisture vapor transmission rates and breathability of the films are useful after the solvents have evaporated.

For gel, medical, shaving, hair removal and cosmetic applications, it has been found that the properties are affected by small changes in the level of water, ratio of NCO/OH, and the level of the di(hydroxymethyl) alkanoic acid. For gel-forming applications such as burn and wound care dressings and drug delivery applications, preferably the amount of water is about 0.01% to about 0.3% and the NCO/OH ratio is from about 0.85 to about 0.98, more preferably the amount of water is from about 0.015% to about 0.25% and the NCO/OH ratio is from about 0.85 to about 0.98, and still more preferably the amount of water level is from about 0.02% to about 0.20% and NCO/OH ratio is from about 0.87 to about 0.98. For high slip, tough, water absorptive coatings and gel-forming polymers with low solubility in water and a weight average molecular weight above about 50,000, preferably the alkanoic acid is from about 0.3% to about 2.5%, the NCO/OH ratio is from about 0.88 to about 0.98, and the amount of water is from about 0.02% to about 0.25%.

For cream and lotion applications such as face creams, moisturizing creams and lotions, urinary rash and baby rash creams and lotions, sun-screen lotions and creams, animal grooming, body and facial hair removal products, shaving preparations, antiperspirants, mascara applications, the polymer is preferably formed from a polyoxyethylene diol having a number average molecular weight of about 4000 to about 12,000, an alkylene glycol, di(hydroxymethyl) alkanoic acid, a preferred amount of water of from about 0.15% to about 0.35%, and a preferred NCO/OH ratio of from about 0.60 to about 0.80. Alternatively, the polymer preferably comprises a polyoxyalkylene diol comprising about 2% to about 10% of a polyoxyethylene diol having a number average molecular weight of about 600 to about 2000 and a polyoxyethylene diol having a number average molecular weight of about 4000 to about 10,000, an amount of water in the reaction mixture from about 0.02% to about 0.35%, and an NCO/OH ratio from about 0.85 to about 0.98. Alternatively, the polymer preferably comprises a polyoxyalkylene diol comprising about minor portion 1% to about 10% of a polyoxypropylene diol having a number average molecular weight of about 400 to about 1200, and a minor portion of about 2% to about 10% of a polyoxyethylene diol having a number average molecular weight of about 600 to about 2000 or a minor portion of about 10% of polyoxyethylene diol having a number average molecular weight of about 600 to about 2000, and about 40% to about 80% of a polyoxyethylene diol having a number average molecular weight of about 4000 to about 10,000, an amount of water in the reaction mixture from about 0.01% to about 0.25%, and an NCO/OH ratio from about 0.84 to about 0.98.

For all aspects of the invention, the urethane forming reaction is preferably catalyzed by known catalysts such as tin salts and organotin esters. Included among the catalysts are stannous octoate, dibutyl tin dilaurate, and tertiary amines such as triethylene diamine, N,N,N',N'-tetramethyl-1,3-butane diamine, preferably tin-containing catalysts, and more preferably stannous octoate and dibutyl tin dilaurate. For the first aspect the most preferred catalyst is stannous octoate, and for aspects two and three, the most preferred catalyst is dibutyl tin dilaurate. The catalyst is used in an amount effective for catalytic reaction, from about 0.001 to 1.0 weight percent of the total weight of the reactive components. Reaction temperature should be controlled from about 40° C. to about 120° C.

The following examples will serve to further typify the nature of this invention but should not be construed as a limitation in scope thereof, which scope is defined solely by the appended claims.

The following examples will serve to further typify the nature of this invention but should not be construed as a limitation in scope thereof, which scope is defined solely by the appended claims.

POLYMER PREPARATION

PRIOR ART HYDROPHILIC POLYURETHANE

EXAMPLE 1

Polyoxyethylene diol having an average molecular weight of 8000 was heated under vacuum to a water level of 0.028% and 744 parts of the dried diol was added to 20.8 parts of diethylene glycol and 0.098 part of water. The mixture was heated with stirring until a homogeneous melt was obtained. Then, 79 parts of methylene bis-cyclohexyl-4-4'-diisocyanate were added during which period the temperature decreased. The NCO/OH ratio was 0.98. When the temperature reached about 65° C., 2.25 ml of dibutyl tin dilaurate was added, and the mass exothermed to about 68° C. The mass was heated at 100° C. for about one hour to complete formation of the polymer. The polymer formed a thick viscous gel at 5% concentration in 55/45 ethanol/water. The viscosity of the hazy gel was 850,000 cps. Addition of dilute ammonia did not clarify the gel and did not visibly affect the viscosity.

EXAMPLE 2

Polyoxyethylene diol having an average molecular weight of 8000 was heated under vacuum to 0.2045% of water, and 744 parts of the dried diol was added to 20.8 parts of diethylene glycol, 18.6 parts of dimethylol propionic acid, and 5.51 parts of water. The mixture was heated with stirring until a homogeneous melt was obtained. Then, 135 parts of methylene bis-cyclohexyl-4-4'-diisocyanate were added during which the temperature decreased. The NCO/OH ratio was 0.50. When the temperature reached about 60° C., 2.25 ml of dibutyl tin dilaurate was added, and the mass was allowed to exotherm to about 65° C. The mass was placed in an oven and held at 100° C. for 1.5 hours to complete formation of the polymer. At 5% concentration, the polymer dissolved in 55/45 ethanol/water to give a milky solution having a viscosity of 11 cps. Upon addition of dilute ammonia, the viscosity did not change and it became clear.

EXAMPLE 3

Polyoxyethylene diol having an average molecular weight of 8000 was heated under vacuum to 0.053% of water, and 473 parts of the dried diol was added to 13.2 parts of diethylene glycol, 11.5 parts of dimethylolpropionic acid, and 0.12 part of water. The mixture was heated with stirring until a homogeneous melt was obtained. Then, 69.7 parts of methylene bis-cyclohexyl-4-4'-diisocyanate were added during which the temperature decreased. The NCO/OH ratio was 0.90. When the temperature reached about 64° C., 0.75 ml of dibutyl tin dilaurate was added. The mass was held at 100° C. for about one hour.

At 5% concentration, the polymer dissolved in 55/45 ethanol/water to give a milky solution having a viscosity of 12 cps. At 5% concentration in 30/65 ethanol/water the viscosity was 34 cps. Upon addition of dilute ammonia, the viscosity of the former solution was 13 cps and that of the latter was 16 cps.

EXAMPLE 4

Polyoxyethylene diol having an average molecular weight of 8000 was heated under vacuum to 0.030% of water, and 744 parts of the dried diol was added to 20.8 parts of diethylene glycol, 18.6 parts of dimethylolpropionic acid, and 0.078 part of water. The mixture was heated with stirring until a homogeneous melt was obtained. Then, 60 parts of methylene bis-cyclohexyl-4-4'-diisocyanate were added. The NCO/OH ratio was 0.50. When the temperature reached about 75° C., 2.25 ml of dibutyl tin dilaurate was added, and the mass was allowed to exotherm. The mass was heated at 100° C. for 1.5 hours. The polymer was dissolved in water at 2% concentration to produce a solution with 4 cps viscosity.

At 5% concentration, the polymer dissolved in 55/45 ethanol/water to give a slightly hazy solution having a viscosity of 9 cps. Upon addition of dilute ammonia, the solution had a viscosity of 7.5 cps, and became clear.

EXAMPLE 5

A batch of 14580 parts of polyoxyethylene diol of 8000 molecular weight was added to a five gallon electrically heated reactor and heated under vacuum to dry the diol. The dried diol was added to 408 parts of diethylene glycol and 356 parts of dimethylolpropionic acid, and the mixture was heated to 105 C in order to melt the ingredients. The mixture was allowed to cool to about 175 F and the water analyzed as 0.20%. Then 40 grams of water was added.

A separate reactor had 2835 parts of methylene bis (cyclohexyl-4-isocyanate). To the diols was added 38 cc of dibutyl tin dilaurate. Then the isocyanate was heated to about 100° F. and the liquids were forced out under nitrogen pressure at about 0.152 ratio. The NCO/OH ratio was 0.85.

The polymer was collected in polypropylene tubs. The polymer was dissolved in 55/42 ethanol/water at 3% to give a viscosity of 24.3 cts. The polymer had a weight average molecular weight of about 130,000. The polymer was insoluble in 60/40 propylene glycol/water at 3% concentration. The polymer was dissolved at 4% concentration in a solution of 75 parts tetrahydrofuran and 25 parts ethanol and a latex rubber Foley catheter was dipped into the solution. The Foley catheter had a slip of 0.053 after two hours of immersion in water. Comparable uncoated catheter had a slip of more than 0.10. The polymer can be used as a high slip coating for guidewires, razors, plastics, polyurethanes, polyethylene, polypropylene, nonwoven cloth, silicone rubber, natural and synthetic rubbers, catheters, knives, medical devices, silicon computer chips, and wires for pacers and bone healing electrical units. The polymer can be used as a filler for bone castings.

EXAMPLE 6

Polyoxyethylene diol having an average molecular weight of 8000 was heated under vacuum to 0.0385% of water, and 744 parts of the dried diol was added to 20.8 parts of diethylene glycol, 18.6 parts of dimethylolpropionic acid, and 0.01 part of water. The mixture was heated with stirring until a homogeneous melt was obtained. Then, 100 parts of methylene bis-cyclohexyl-4-4'-diisocyanate were added. The NCO/OH ratio was 0.85. When the temperature reached about 68° C., 2.25 ml of dibutyl tin dilaurate was added and the mass exothermed. The mass was heated at 100° C. for 1.5 hours to complete formation of the polymer.

At 2.0% concentration of the polymer in water, the slightly hazy solution had a viscosity of 9 cps and at 2.5% it had viscosity of 11.2 cps. At 5% concentration, the polymer dissolved in 55/45 ethanol/water to give a hazy solution having a viscosity of 11 cps. At 5% concentration in 30/65 ethanol/water the slightly hazy solution had a viscosity was 19 cps. Upon addition of dilute ammonia to bring the pH to 9.0, the viscosity of the former was 11.5 cps and that of the latter was 12.5 cps. Both solutions were clear.

EXAMPLE 7

Polyoxyethylene diol having an average molecular weight of 8000 was heated under vacuum to 0.048% of water, and 744 parts of the dried diol was added to 21 parts of diethylene glycol, 38 parts of dimethylolpropionic acid, and 0.071 part of water. The mixture was heated with stirring until a homogeneous melt was obtained. Then, 132 parts of methylene bis-cyclohexyl-4-4'-diisocyanate were added. The NCO/OH ratio was 0.85. When the temperature reached about 73° C., 2.25 ml of dibutyl tin dilaurate was added. The mass was heated at 100° C. for 1.5 hours to complete formation of the polymer.

The polymer dissolved at 2.0% concentration in water and the solution had a viscosity of 9.5 and at 2.5% concentration the viscosity was 13.5 cps. Both solutions had a slight haze. At 5% concentration, the polymer dissolved in 55/45 ethanol/water to give a viscosity of 10 cps and at 5% in 30/65 ethanol/water, for a viscosity of 20 cps. Both solutions were hazy. Dilute ammonia was added to increase the pH to 9. The viscosity of the former was 10 and that of the latter was 13 cps. Both solutions were clear.

EXAMPLE 8

Polyoxyethylene diol having an average molecular weight of 8000 was heated under vacuum to 0.050% of water, and 474 parts of the dried diol was added to 13 parts of diethylene glycol, 12 parts of dimethylolpropionic acid, and 0.15 part of water. The mixture was heated with stirring until a homogeneous melt was obtained. Then, 73 parts of methylene bis-cyclohexyl-4-4'-diisocyanate were added. The NCO/OH ratio was 0.94. When the temperature reached about 61° C., 1.5 ml of dibutyl tin dilaurate was added. The mass was heated at 100° C. for about one hour.

The polymer was dissolved at 5% concentration in 55/45 and 30/65 ethanol/water, giving viscosities of 12.0 and 23.5 cps, respectively. When the pH was raised with dilute ammonia, the viscosities were 9 and 14.4 cps, respectively,

EXAMPLE 9

Polyoxyethylene diol having an average molecular weight of 8000 was heated under vacuum to 0.088% of water, and 744 parts of the dried diol was added to 21 parts of diethylene glycol, 4.3 parts of dimethylolpropionic acid, and 0.020 part of water. The mixture was heated with stirring until a homogeneous melt was obtained. Then, 81 parts of methylene bis-cyclohexyl-4-4'-diisocyanate were added. The NCO/OH ratio was 0.85. When the temperature reached about 61° C., 2.25 ml of dibutyl tin dilaurate was added, and the mass was allowed to exotherm. The mass was heated at 100° C. for about one hour to complete formation of the polymer. At a 5% concentration the polymer dissolved in 55/45 ethanol water to give a solution with a viscosity of 127 cps and 2 cc of dilute ammonia in 180 grams reduced the viscosity to 69 cps. Both solutions had very small amounts of insolubles.

EXAMPLE 10

Polyoxyethylene diol having an average molecular weight of 8000 was heated under vacuum to 0.037% of water, and 744 parts of the dried diol was added to 21 parts of diethylene glycol, 19 parts of dimethylolpropionic acid, and 0.023 part of water. The mixture was heated with stirring until a homogeneous melt was obtained. Then, 115 parts of methylene bis-cyclohexyl-4-4'-diisocyanate were added. The NCO/OH ratio was 0.98. When the temperature reached about 65° C., 2.25 ml of dibutyl tin dilaurate was added, and the mass was allowed to exotherm. The mass was heated at 100° C. for about one hour to complete the polymerization.

At 5% concentration, the polymer dissolved in 55/45 ethanol/water to give a clear solution with 5 pH and a viscosity of 1680 cps. Adding 2 cc dilute ammonia to 180 grams of solution reduced the viscosity of 225 cps. Both solutions were clear. Sodium bicarbonate also clarified the solution.

EXAMPLE 11

Polyoxyethylene diol having an average molecular weight of 8000 was heated under vacuum to 0.208% of water, and 744 parts of the dried diol was added to 21 parts of diethylene glycol, 19 parts of dimethylolpropionic acid, and 2.90 part of water. The mixture was heated until a homogeneous melt was obtained. Then, 106 parts of methylene bis-cyclohexyl-4-4'-diisocyanate were added. The NCO/OH ratio was 0.50. When the temperature was about 63° C., 2.25 ml of dibutyl tin dilaurate was added. The mass was allowed to exotherm, and then heated at 100° C. for 1.5 hours. At a concentration of 5% in 55/45 ethanol/water, the polymer produced a milky solution having a viscosity of 12.5 cps, and at 5% in 30/60 ethanol/water the milky solution had a viscosity of 15.0 cps. Both solutions became clear upon the addition of dilute ammonia, with viscosities of 14 and 13 cps, and solutions of 2% and 2.5% polymer in water had viscosities of 4.5 and 7.0 cps, respectively.

EXAMPLE 12

Polyoxyethylene diol having an average molecular weight of 8000 and polyoxyethylene diol having an average molecular weight of 1450 were heated under vacuum to 0.107% of water, and 1105 parts of the dried diol was added to 83 parts of ethylene glycol, 193 parts of dimethylolpropionic acid, and 1.485 part of water. The mixture was heated with stirring until a homogeneous melt was obtained. Then, 888 parts of methylene bis-cyclohexyl-4-4'-diisocyanate were added. The NCO/OH ratio was 0.93. When the temperature reached about 59° C., 3.0 ml of stannous octoate was added, and the mass was allowed to exotherm. The mass was heated at 100° C. for about one hour to complete formation of the polymer. The solutions had viscosities of 4.5 and 7.0 cps. About 5% polymer in 55/45 ethanol/water gave a partial solution of polymer; particles were noted floating in the solvent. The solution had a viscosity of 12.5 cps. Upon addition of dilute ammonia, the viscosity was 14 cps and the solution was clear.

EXAMPLE 13

Polyoxyethylene diol having an average molecular weight of 8000 was heated under vacuum to 0.271% of water, and 736 parts of the dried diol was added to 21 parts of diethylene glycol, 38 parts of dimethylolpropionic acid, and 0.271 part of water. The mixture was heated with stirring until a homogeneous melt was obtained. Then, 145 parts of methylene bis-cyclohexyl-4-4'-diisocyanate were added. The NCO/OH ratio was 0.75. When the temperature reached about 59° C., 1.85 ml of dibutyl tin dilaurate was added, and the mass was allowed to exotherm. The mass was heated at 100° C. for about one hour to complete formation of the polymer. At a concentration of 5%, the polymer formed a milky solution in 55/45 ethanol/water having a viscosity of 9.0 cps. The mixture was made basic with dilute ammonia to provide a water clear solution having a viscosity of 15.3 cps. The polymer can be used as an anti-graffiti coating and for use in cosmetic applications including shaving preparations, facial and body hair removal products, animal grooming products and antiperspirants.

EXAMPLE 14

Polyoxyethylene diol having an average molecular weight of 8000 was heated under vacuum to 0.276% of water, and 736 parts of the dried diol was added to 21 parts of diethylene glycol, 24 parts of dimethylolpropionic acid, and 0.270 part of water. The mixture was heated with stirring until a homogeneous melt was obtained. Then, 124 parts of methylene bis-cyclohexyl-4-4'-diisocyanate were added. The NCO/OH ratio was 0.75. When the temperature reached about 56° C., 1.85 ml of dibutyl tin dilaurate was added, and the mass was allowed to exotherm. The mass was heated at 100° C. for about one hour to complete formation of the polymer. The polymer formed a milky solution in 55/45 ethanol/water at a concentration of 5%. The pH was 5.0 and the viscosity was 9.0 cps. The pH of about 20 cc of solution was increased to about 7 with dilute ammonia, potassium hydroxide, sodium bicarbonate, and lithium acetate dihydrate. The slightly basic solutions were water clear, and the viscosity of solution with ammonia was 15 cps. The polymers can be used in anti-graffiti coatings, and cosmetic applications including shaving preparations, facial and body hair removal products and antiperspirants.

EXAMPLE 15

Polyoxyethylene diol having an average molecular weight of 1450 (C1400) was heated under vacuum to a water level of 0.244% and 227 parts of the dried diol was added to 156 parts of polyoxyethylene diol having an average molecular weight of 1000, 94 parts of polyoxyethylene diol having an average molecular weight of 600 (C600), 62 parts of polyoxyethylene diol having an average molecular weight of 400 (C400), 120 parts of ethylene glycol, 381 parts of polyoxytetramethylene glycol having an average molecular weight of 2000 (TR2000), 104 parts of polyoxypropylene glycol having an average molecular weight of 1025 (C1025), 93 parts of dimethylolpropionic acid, and 4.51 parts of water. The mixture was heated with stirring until a homogeneous melt was obtained. Then, 1026 parts of methylene bis-cyclohexyl-4-4'-diisocyanate were added. The NCO/OH ratio was 0.98. When the temperature reached about 50° C., 3.4 ml of stannous octoate ($T_9$) was added, and the mass was allowed to exotherm. The mass was heated at 100° C. for about one hour to complete formation of the polymer. The polymer had a tear strength of 520 pounds per inch, and modulus at 100% elongation of 1470 pounds per square inch compared to values of 260 pounds/inch and 670 pounds per square inch for a similar polymer made without dimethylolpropionic acid. The polymer had a water content of 21% and a linear expansion of 8% after exposure to water and similar polymer without any dimethylolpropionic acid had corresponding values of 25% and 11%. The polymer was dissolved in 75/25 tetrahydrofuran/ethanol to give a viscosity of 15 cps. Upon the addition of 5% water, the viscosity increased to 6120 cps. The polymer can be used as a thickener in creams, lotions and foams.

EXAMPLE 16

Polyoxyethylene diol having an average molecular weight of 8000 and polyoxyethylene diol having an average molecular weight of 1450 were heated under vacuum to 0.2075% of water, and 269 parts of the 8000 and 114 parts of the higher molecular weight glycol were added to 12 parts of diethylene glycol, 18 parts of dimethylolpropionic acid, and 0.10 part of water. The mixture was heated with stirring until a homogeneous melt was obtained. Then, 88 parts of methylene bis-cyclohexyl-4-4'-diisocyanate were added. The NCO/OH ratio was 0.92. When the temperature reached about 65° C., stannous octoate was added, and the mass was allowed to exotherm. The mass was heated at 100° C. for about one hour to complete formation of the polymer. The polymer dissolved in slightly basic 55/45 ethanol/water at a concentration of 5% to produce a clear solution with a viscosity of 12 cps. The solution was poured on a glass plate to form a film. The film required more force to remove from the glass plate than did a similar film made from Example 1. The film of this example did not dissolve in water but was readily removed by a solution of sodium bicarbonate in water. The polymers can be used as anti-graffiti coatings and as coatings in paint booths.

EXAMPLE 17

A batch of 325 parts of polyoxytetramethylene diol having an average molecular weight of 2000, 89 parts of polyoxypropylene diol having an average molecular weight of 1025, 194 parts of polyoxyethylene diol having an average molecular weight of 1450, 134 parts of polyoxyethylene diol having an average molecular weight of 1000, 80 parts of polyoxyethylene diol having an average molecular weight of 600, 53 parts of polyoxyethylene diol having an average molecular weight of 400, 103 parts of ethylene glycol, 37 parts of dimethylolpropionic acid, and 6.44 parts of water was heated with stirring until a homogeneous melt was obtained. Then, 795 parts of methylene bis-cyclohexyl-4-4'-diisocyanate were added. The NCO/OH ratio was 0.98. When the temperature reached about 45° C., 2.75 ml of stannous octoate was added, and the mass was allowed to exotherm. The mass was heated at 100° C. for about one hour to complete formation of the polymer. The polymer had a tensile strength of 4740 pounds per square inch, an elongation of 340%, and a 100% modulus of 1000 pounds per square inch. The polymer had a water content of 25% and linear expansion of 11% after exposure to water. A comparable polymer made without dimethylolpropionic acid had a tensile strength of 3510 pounds per square inch, an elongation of 340%, a 100% modulus of 670 pounds per square inch, and a water content of 25% and a linear expansion of 11% after exposure to water.

The polymers can be used as appetite suppressants, since they can bond amines, as hydrophilic breathable adhesive films, and as adhesives in electroconductive surgical pads. The polymer was dissolved in 75/25 tetrahydrofuran/ethanol to give a viscosity of 15 cps. Upon the addition of 5% water, the viscosity increased to 6120 cps.

EXAMPLE 18

Polyoxyethylene diol having an average molecular weight of 8000 was heated under vacuum to 0.156% of water and 756 parts of the dried diol was added to 21 parts of diethylene glycol, 39 parts of dimethylolpropionic acid, and 0.25 part of water. The mixture was heated with stirring until a homogeneous melt was obtained. Then, 136 parts of methylene bis-cyclohexyl-4-4'-diisocyanate were added. The NCO/OH ratio was 0.75. When the temperature reached about 66° C., 1.85 ml of dibutyl tin dilaurate was added, and the mass was allowed to exotherm. The mass was heated at 100° C. for about one hour to complete formation of the polymer. The polymer dissolved in a slightly basic 55/45 ethanol/water solution at a concentration of 5% to produce a clear solution with a viscosity of 11 cps. The polymer was used to make an excellent film with improved breathability, washability, adhesion, and moisture vapor transmission rate and the polymer can be used in cosmetic applications including shaving preparations, facial and body hair removal products, and antiperspirants, and to promote a healthy skin.

EXAMPLE 19

Polyoxyethylene diol having an average molecular weight of 8000 was heated under vacuum to 0.032% of water and 736 of the dried diol was added to 21 parts of diethylene glycol, 18 parts of dimethylolpropionic acid, and 2.06 parts of water. The mixture was heated with stirring until a homogeneous melt was obtained. Then, 113 parts of methylene bis-cyclohexyl-4-4'-diisocyanate were added. The NCO/OH ratio was 0.75. When the temperature reached about 65° C., 1.85 ml of dibutyl tin dilaurate was added, and the mass was allowed to exotherm. The mass was heated at 100° C. for about one hour to complete formation of the polymer. The polymer dissolved in a slightly basic 55/45 ethanol/water solution at a concentration of 5% to produce a clear solution with a viscosity of 13 cps. The polymer had a kinematic viscosity of 6.50 cts in 55/42/3 ethanol/water/polymer solution. The polymer can be used in cosmetic applications including shaving creams, lotions, and foams, facial and body hair removal products, and antiperspirants. The cosmetic films had improved breathability, washability, adhesion, and moisture vapor and oxygen transmission rate and can be used to maintain a healthy skin due its excellent breathability properties.

EXAMPLE 20

Polyoxyethylene diol having an average molecular weight of 8000 was heated under vacuum to 0.060% of water and 736 parts of the dried diol was added to 21 parts of diethylene glycol, 18 parts of dimethylolpropionic acid, and 2.84 parts of water. The mixture was heated with stirring until a homogeneous melt was obtained. Then, 139 parts of methylene bis-cyclohexyl-4-4'-diisocyanate were added. The NCO/OH ratio was 0.85. When the temperature reached about 64° C., 1.85 ml of dibutyl tin dilaurate was added, and the mass was allowed to exotherm. The mass was heated at 100° C. for about one hour to complete formation of the polymer. The polymer had a molecular weight of 76,000 and dissolved in a slightly basic 55/45 ethanol/water solution at a concentration of 5% to give a viscosity of 18 cps. The polymer had a kinematic viscosity of 14.7 cts in 55/42/3 ethanol/water/polymer solution. The polymer was used in cosmetic applications including shaving creams, lotions, and foams, facial and body hair removal products, and antiperspirants. The polymer can be used in animal grooming products. The polymeric film had improved breathability and moisture vapor transmission rate which promotes a healthy skin.

EXAMPLE 21

Polyoxyethylene diol having an average molecular weight of 8000 was heated under vacuum to 0.074% of water and 281 parts added to 7.9 parts of diethylene glycol, 55 parts of dimethylolpropionic acid, and 1.38 parts of water. The mixture was heated with stirring until a homogeneous melt was obtained. Then, 109 parts of methylene bis-cyclohexyl-4-4'-diisocyanate were added. The NCO/OH ratio was 0.65. When the temperature reached about 70° C., 0.68 ml of dibutyl tin dilaurate was added, and the mass was allowed to exotherm. The mass was heated at 100° C. for about one hour to complete formation of the polymer. The polymer dissolved in a slightly basic 55/45 ethanol/water solution at a concentration of 5% to produce a clear solution with a viscosity of 10 cps. The polymer can be used in cosmetic products including shaving preparations, facial and body hair removal products, animal grooming products, creams and antiperspirants. The hydrophilic film had improved breathability and moisture vapor transmission rate which are valuable in promoting healthy skin.

EXAMPLE 22

Polyoxyethylene diol having an average molecular weight of 8000 was heated under vacuum to 0.099% of water and 306 parts of the dried diol was added to 34 parts of a block copolymer of ethylene oxide and propylene oxide made by BASF under the tradename of F127, 9.5 parts of diethylene glycol, 27 parts of dimethylolpropionic acid, and 1.30 parts of water. The mixture was heated with stirring until a homogeneous melt was obtained. Then, 77 parts of methylene bis-cyclohexyl-4-4'-diisocyanate were added. The NCO/OH ratio was 0.65. When the temperature reached about 67° C., 0.68 ml of dibutyl tin dilaurate was added, and the mass was allowed to exotherm. The mass was heated at 100° C. for about one hour to complete formation of the polymer. The polymer can be dissolved in slightly basic 55/45 ethanol/water at a concentration of 5% to produce a clear solution with a viscosity of less than 20 cps.

EXAMPLE 23

Polyoxyethylene diol having an average molecular weight of 8000 was heated under vacuum to 0.072% of water, and 343 parts of the dried diol was added to 18 parts of polyoxypropylene glycol of 425 molecular weight, 10 parts of diethylene glycol, 18 parts of dimethylolpropionic acid, and 0.43 part of water. The mixture was heated with stirring until a homogeneous melt was obtained. Then, 79 parts of methylene bis-cyclohexyl-4-4'-diisocyanate were added. The NCO/OH ratio was 0.85. When the temperature reached about 58° C., 0.68 ml of dibutyl tin dilaurate was added, and the mass was allowed to exotherm. The mass was heated at 100° C. for about one hour to complete formation of the polymer. The polymer dissolved in 55/45 ethanol/water at a concentration of 5% to produce a clear solution with a viscosity of 12 cps. The polymer can be used to make an improved cosmetic products including shaving preparations, facial and body hair removal products, and antiperspirants.

EXAMPLE 24

Polyoxyethylene diol having an average molecular weight of 8000 was heated under vacuum to 0.061% of water, and 736 parts of the dried diol was added to 21 parts of diethylene glycol, 59 parts of dimethylolpropionic acid, and 1.11 part of water. The mixture was heated with stirring until a homogeneous melt was obtained. Then, 185 parts of methylene bis-cyclohexyl-4-4'-diisocyanate were added. NCO/OH ratio was 0.85. When the temperature reached about 63° C., 1.85 ml of dibutyl tin dilaurate was added, and the mass was allowed to exotherm. The mass was heated at 100° C. for about one hour to complete formation of the polymer. The polymer had a molecular weight of 21,000 and dissolved in slightly basic 55/45 ethanol/water solution at a concentration of 5% was clear and had a viscosity of 10 cps. The polymer had a kinematic viscosity of 6.15 cts in 55/42/3 ethanol/water/polymer solution. The polymer can be used in cosmetic applications including creams and lotions, moisturizing lotions and creams, shaving preparations, facial and body hair removal products, depilatories, and antiperspirants. The hydrophilic film had improved breathability and can be used to promote a healthy skin.

EXAMPLE 25

Polyoxyethylene diol having an average molecular weight of 8000 was heated under vacuum to 0.215% of water, and 736 parts of the dried diol was added to 21 parts of diethylene glycol, 59 parts of dimethylolpropionic acid, and 1.81 parts of water. The mixture was heated with stirring until a homogeneous melt was obtained. Then, 168 parts of methylene bis-cyclohexyl-4-4'-diisocyanate were added. NCO/OH ratio was 0.65. When the temperature reached about 70° C., 1.85 ml of dibutyl tin dilaurate was added, and the mass was allowed to exotherm. The mass was heated at 100° C. for about one hour to complete formation of the polymer. The polymer had a molecular weight of 15,000 and dissolved in slightly basic 55/45 ethanol/water solution at a concentration of 5% was clear and had a viscosity of 10 cps. The polymer had a kinematic viscosity of 4.60 cts in 55/42/3 ethanol/water/polymer solution. The polymer can be used in to give superior cosmetic products including shaving lotions, creams and foams, moisturizing lotions and creams, facial creams, animal grooming products, facial and body hair removal products, and antiperspirants, and superior coatings of guidewires, catheters, plastics, elastomers, polyolefins, silicone rubber, metals, steel, brass, silicon, bronze and polyurethane to enhance slip and biocompatibility. The coatings are useful in industrial applications, and medical devices. The cosmetic films had improved washability, adhesion to skin, breathability, a soft feel, and promote a healthy skin.

EXAMPLE 26

Polyoxyethylene diol having an average molecular weight of 8000 was heated under vacuum to 0.060% of water, and 736 parts of the dried diol was added to 21 parts of diethylene glycol, 18 parts of dimethylolpropionic acid, and 0.96 part of water. The mixture was heated with stirring until a homogeneous melt was obtained. Then, 114 parts of methylene bis-cyclohexyl-4-4'-diisocyanate were added. NCO/OH ratio was 0.85. When the temperature reached about 63° C., 1.85 ml of dibutyl tin dilaurate was added, and the mass was allowed to exotherm. The mass was heated at 100° C. for about one hour to complete formation of the polymer. The polymer dissolved in slightly basic 55/45 ethanol/water solution at a concentration of 5% was clear and had a viscosity of 14 cps. The polymer had a molecular weight of 40,000 and can be used to give superior cosmetic products including shaving lotions, creams and foams, moisturizing lotions and creams, facial creams, animal grooming products, facial and body hair removal products, and antiperspirants, and in coatings of guidewires, catheters, metals, plastics, elastomers, including polyolefins, silicon, polystyrene, silicone rubber, polyurethane, steel, brass, bronze to enhance slip and biocompatibility. The high-slip coatings are useful in medical devices. Polymeric films had excellent breathability and promote a healthy skin.

EXAMPLE 27

Polyoxyethylene diol having an average molecular weight of 8000 was heated under vacuum to 0.060% of water, and 336 parts of the dried diol was added to 9.3 parts of diethylene glycol, 27 parts of dimethylolpropionic acid, 8.2 parts of diglycolamine and 0.002 part of water. The mixture was heated with stirring until a homogeneous melt was obtained. Then, 73 parts of methylene bis-cyclohexyl-4-4'-diisocyanate were added. NCO/OH ratio was 0.65. When the temperature reached about 65° C., 0.92 ml of dibutyl tin dilaurate was added, and the mass was allowed to exotherm. The mass was heated at 100° C. for about one hour to complete formation of the polymer. The polymer dissolved in slightly basic 55/45 ethanol/water solution at a concentration of 5% was clear. The polymer had a kinematic viscosity of 5.93 cts in 55/42/3 ethanol/water/polymer solution. The polymer can be used in cosmetic applications including shaving preparations, depillatories, and antiperspirants. Cosmetic films had excellent breathability, washability and adhesion, and promote a healthy skin.

EXAMPLE 28

Polyoxyethylene diol having an average molecular weight of 8000 and polyoxyethylene diol having an average molecular weight of 1450 were heated under vacuum to 0.132% of water, and 291 parts of the higher molecular weight dried diol and 15.3 parts of lower molecular weight dried diol were added to 9.5 parts of dipropylene glycol, 27 parts of dimethylolpropionic acid, 34 parts of polyoxypropylene glycol of 425 molecular weight, and 1.146 part of water. The mixture was heated with stirring until a homogeneous melt was obtained. Then, 89 parts of methylene bis-cyclohexyl-4-4'-diisocyanate were added. NCO/OH ratio was 0.65. When the temperature reached about 67° C., 0.68 ml of dibutyl tin dilaurate was added, and the mass was allowed to exotherm. The mass was heated at 100° C. for about one hour to complete formation of the polymer. The polymer dissolved in slightly basic 55/45 ethanol/water solution at a concentration of 5% was clear and had a viscosity of 8 cps. The polymer can be used to give superior cosmetic products such as shaving preparations, facial and body hair removal products, and antiperspirants. The cosmetic films had excellent breathability, washability, adhesion, and promote a healthy skin.

EXAMPLE 29

A batch of 13147 parts of polyoxethylene diol having an average molecular weight of 8000 was added to a five-gallon electrically heated reactor and heated under vacuum to dry the glycol. The dried diol was added to 368 parts of diethylene glycol and 321 parts of dimethylolpropionic acid, and the mixture was heated to 105° C. in order to melt the ingredients. The mixture was allowed to cool to about 175° F. to about 185° F. and the water level was analyzed by Karl Fisher method as 0.0675%. Then, 19.41 grams of water was added to the mixture to bring the total water to 28.75 grams of water.

A separate reactor contained 2073 parts of methylene bis(cyclohexyl-4-isocyanate). To the diols was added 33.04 cc of dibutyl tin dilaurate. Then the isocyanate was heated to about 110°–115° F., and both liquids were forced out under nitrogen pressure using a piston cylinder at about a ratio of 0.1492. Twelve shots of liquid were pumped into a polypropylene tub and heated for one hour at 100° C. The NCO/OH ratio was 0.85.

The polymer was dissolved at 3% solids in 55/45/5 ethanol/water/polymer solution and gave viscosities of 11 cps using a Brookfield viscometer. The polymer had a kinematic viscosity of 7.67 cts in 55/42/3 ethanol/water/polymer solution. The polymer had a molecular weight of 40,000.

The polymer can be used in cosmetic applications including shaving lotions, creams and foams, moisturizing lotions and creams, facial creams, animal grooming products, facial and body hair removal products, and antiperspirants, and in coatings of guidewires, catheters, metals, plastics, elastomers, including polyolefins, silicon, polystyrene, silicone rubber, polyurethane, steel, brass, bronze to enhance slip, adhesion and biocompatibility. The coatings are useful in industrial applications and medical devices.

EXAMPLE 30

A batch of 13147 parts of polyoxethylene glycol having an average molecular weight of 8000 was added to a five-gallon electrically heated reactor and heated under vacuum to dry the glycol. The dried diol was added to 368 parts of diethylene glycol and 321 parts of dimethylolpropionic acid, and the mixture was heated to 105° C. in order to melt the ingredients The mixture was allowed to cool to about 175° F. to about 185° F. and a sample of the mixture was taken and analyzed for its water content by Karl Fisher method. The mixture had a water content of 0.0625% water and 26.66 grams of water was added to the mixture to bring the total water to 35.31 grams of water.

A separate reactor contained 2162 parts of methylene bis(cyclohexyl-4-isocyanate). To the diols was added 33.04 cc dibutyl tin dilaurate. Then the diisocyanate was heated to about 110°–115° F., and both liquids were forced out under nitrogen pressure using a piston cylinder at about a ratio of 0.1555. Twelve shots of liquid were pumped into a polypropylene tub and heated for one hour at 100° C. The NCO/OH ratio was 0.85.

The polymer was dissolved at 3% solids in 55/45/5 ethanol/water/polymer solution and gave viscosities of 11.5 cps using a Brookfield viscometer. The polymer had a kinematic viscosity of 9.81 cts in 55/42/3 ethanol/water/polymer solution. and a molecular weight of 49,000.

The polymer can be used in cosmetic applications such as shaving lotions, creams and foams, moisturizing lotions and creams, facial creams, urinary and baby rash creams and lotions, animal grooming products, facial and body hair removal products, and antiperspirants, and in coatings of guidewires, catheters, metals, plastics, elastomers, including polyolefins, silicon, polystyrene, silicone rubber, polyurethane, steel, brass, bronze to enhance slip, adhesion and biocompatibility. The coatings are useful in industrial applications and in medical devices.

EXAMPLE 31

Polyoxyethylene diol having an average molecular weight of 8000 was heated under vacuum to 0.028% of water, and 736 parts of the dried diol was added to 21 parts of cyclohexanedimethanol, 18 parts of dimethylolpropionic acid, and 1.21 parts of water. The mixture was heated with stirring until a homogeneous melt was obtained. Then, 102 parts of methylene bis-cyclohexyl-4-4'-diisocyanate were added. NCO/OH ratio was 0.85. When the temperature reached about 65° C., 1.85 ml of dibutyl tin dilaurate was added, and the mass was allowed to exotherm. The mass was heated at 100° C. for about one hour to complete formation of the polymer. The polymer can be dissolved in slightly basic 55/45 ethanol/water solution at a concentration of 5% to give a low viscosity clear solution. The polymer can be used in cosmetic applications including shaving lotions, creams and foams, moisturizing lotions and creams, facial creams, animal grooming products, facial and body hair removal products, and antiperspirants, and in coatings of guidewires, catheters, metals, plastics, elastomers, including polyolefins, silicon, polystyrene, silicone rubber, polyurethane, steel, brass, bronze to enhance slip, adhesion and biocompatibility. The coatings are useful in industrial applications and in medical devices.

EXAMPLE 32

Polyoxyethylene diol having an average molecular weight of 8000 was heated under vacuum to 0.048% of water and 744 parts of the dried diol was added to 21 parts of diethylene glycol, 4.3 parts of dimethylolpropionic acid, and 0.37 part of water. The mixture was heated with stirring until a homogenous melt was obtained. Then, 88 parts of methylene bis-cyclohexyl-4-4'-diisocyanate were added. The NCO/OH ratio was about 0.98. When the temperature reached abut 65 C, 2.25 ml of dibutyl tin dilaurate was added, and the mass was allowed to exotherm. The mass was heated at 100 C for about one hour to complete formation of the polymer. The polymer had a weight average molecular weight of 141,000. At a 5% concentration the polymer dissolved in 55/45 ethanol water to give a solution with a viscosity of 180 cps. At a concentration of 3% in 60/40 propylene glycol/water, the solution had a viscosity of 5300 cps. A gel made with 19% of polymer in 20/80 propylene glycol/water was tough, exceptionally clear and adhered to the glass. The viscosity of the gel can be reduced by raising the pH above 7.0. Gels containing lower concentrations of polymer can be used to keep wounds and burns moist during the healing process. The polymer was dissolved at 4% concentration in 75/25 tetrahydrofuran/ethanol and a latex rubber Foley catheter was dipped into the solution. The Foley catheter had a slip of 0.053 after two hours of immersion in water. Comparable uncoated catheter had a slip of more than 0.10. The polymer can be used as a high slip and biocompatible coating for guidewires, razors, catheters, silicon computer chips, and wires for bone healing electrical units. The polymers can be used in shaving lotions, creams and foams, moisturizing and facial lotions and creams, animal grooming products, depillatories and antiperspirants, and in coatings of metals, elastomers and plastics including polyolefins, polystyrene, silicone rubber, polyurethane, steel, brass, bronze to enhance slip, adhesion and biocompatibility. The coatings are useful in industrial applications and medical devices. The polymer can be used as a filler for bone castings.

EXAMPLE 33

Polyoxyethylene diol having an average molecular weight of 8000 was heated under vacuum to 0.037% of water and 744 parts of the dried diol was added to 21 parts of diethylene glycol, 18.6 parts of dimethylol propionic acid, and 0.23 part of water. The mixture was heated with stirring until a homogeneous melt was obtained. Then, 115 parts of methylene bis-cyclohexyl-4-4'-diisocyanate were added. The NCO/OH ratio was about 0.98. When the temperature reached abut 65 C, 2.25 ml of dibutyl tin dilaurate was added, and the mass was allowed to exotherm. The mass was heated at 100 C for about one hour to complete formation of the polymer. The polymer had a weight average molecular weight of 63,000. At a 5% concentration the polymer dissolved in 55/45 ethanol water to give a solution with a viscosity of 1680 cps, and a reduced viscosity of 225 cps upon the addition of 2 cc ammonia to 180 grams of the solution. At a concentration of 3% in 60/40 propylene glycol/water, the solution had a viscosity of 144 cps. A gel made with 19% of polymer in 20/80 propylene glycol/water was tough, exceptionally clear, and adhered to the glass, displaying improved adhesive properties compared to gels made using polymer without the alkanoic acid. Gels containing lower concentrations of polymer can be used to keep wounds and burns moist during the healing process. The polymer can be used as a high slip coating for guidewires, razors, catheters, silicon computer chips, wires for bone healing electrical units. The polymers can be used in shaving lotions, creams and foams, moisturizing lotions and creams, facial creams, animal grooming products, facial and body hair removal products, and antiperspirants, and in coatings of metals, plastics, elastomers, including polyolefins, polystyrene, silicone rubber, polyurethane, steel, brass, bronze to enhance slip, adhesion and biocompatibility. The coatings are useful in industrial applications and in medical devices. The polymer can be used as a filler for bone castings.

EXAMPLE 34

Polyoxyethylene diol having an average molecular weight of 8000 was heated under vacuum to 0.062% of water and 470 parts of the dried diol was added to 13.2 parts of diethylene glycol, 11.4 parts of dimethylol propionic acid, and 0.55 part of water. The mixture was heated with stirring until a homogenous melt was obtained. Then, 76 parts of methylene bis-cyclohexyl-4-4'-diisocyanate were added. The NCO/OH ratio was about 0.90. When the temperature reached about 61 C, 1.44 ml of dibutyl tin dilaurate was added, and the mass was allowed to exotherm. The mass was heated at 100 C for about one hour to complete formation of the polymer. The polymer had a weight average molecular weight of 46,000. At a 5% concentration the polymer dissolved in 55/45 ethanol water to give a solution with a viscosity of 13 cps, and a reduced viscosity of 12 cps upon the addition of 2 cc ammonia to 180 grams of the solution. At a concentration of 3% in 60/40 propylene glycol/water, the solution had a viscosity of 64 cps. At a concentration of 5% in 30/70 ethanol/water, the solution had a viscosity of 34 cps, and upon neutralization, the viscosity dropped to 16 cps. A gel made with 19% of polymer in 20/80 propylene glycol/water was tough, exceptionally clear, and adhered to the glass, displaying improved adhesive properties compared to gels made using polymer without the alkanoic acid. Gels containing lower concentrations of polymer can be used to keep wounds and burns moist during the healing process. The polymer can be used as a high slip coating for guidewires, razors, catheters, silicon computer chips, wires for bone healing electrical units. The polymers can be used in shaving lotions, creams and foams, moisturizing lotions and creams, facial creams, animal grooming products, facial and body hair removal products, and antiperspirants, and in coatings of metals, plastics, elastomers, including polyolefins, polystyrene, silicone rubber, polyurethane, steel, brass, bronze to enhance slip, adhesion and biocompatibility. The coatings are useful in industrial applications and in medical devices. The polymer can be used as a filler for bone castings.

EXAMPLE 35

A batch of 13111 parts of polyoxyethylene diol of 8000 molecular weight was added to a five gallon electrically heated rector and heated under vacuum to dry the glycol. The dried diol was added to 367 parts of diethylene glycol and 320 parts of dimethylolpropionic acid, and the mixture was heated to 105 C in order to melt the ingredients. The mixture was allowed to cool to about 175 F and the water analyzed as 0.14%. Then 5.64 grams of water was added.

A separate reactor had 2109 parts of methylene bis(cyclohexyl-4-isocyanate). To the diols was added 133 cc of dibutyl tin dilaurate. Then the isocyanate was heated to about 100 F and the liquids were forced out under nitrogen pressure at about 0.152 ratio. The NCO/OH ratio was 0.89.

The polymer was collected in polypropylene tubs. The polymer was dissolved in 55/45 ethanol/water at 5% to give a viscosity of 25 cps. The polymer was dissolved at 5% concentration in 30/70 ethanol/water to give a viscosity of 3000 cps which dropped to 205 cps upon the addition of a few cc of ammonia to raise the pH. The polymer was dissolved in 60/40 propylene glycol/water at 3% concentration to give a viscosity of about 166 cps, and the polymer formed a tough exceptionally clear gel at 19% concentration in 20/80 propylene glycol/water with improved adhesion for use in burn and wound care dressings, pre- and post-shaving preparations. Gels containing lower concentrations of polymer can be used to keep wounds and burns moist during the healing process. The polymer can be used as a high slip coating for guidewires, razors, catheters, knives, silicon computer chips, and wires for pacers and bone healing electrical units. The polymers can be used in shaving lotions, creams and foams, moisturizing lotions and creams, facial creams, animal grooming products, facial and body hair removal products, and antiperspirants, and in coatings of metals, plastics, elastomers, including polyolefins, polystyrene, silicone rubber, polyurethane, steel, brass, bronze to enhance slip, adhesion and biocompatibility. The coatings are useful in industrial applications and in medical devices. The polymer can be used as a filler for bone castings.

EXAMPLE 36

Polyoxyethylene diol having an average molecular weight of 8000 was heated under vacuum to reduce the water level, and 734 parts of the dried diol was added to 52 parts of polyoxyethylene diol having a number average molecular weight of 1450, 49 parts of polyoxypropylene diol having a number average molecular weight of 425, and 4.5 parts of dimethylol propionic acid, and sufficient water to bring the total to 0.31 part. The mixture was heated with stirring until a homogenous melt was obtained. Then, 69 parts of methylene bis-cyclohexyl-4-4'-diisocyanate were added. The NCO/OH ratio was about 0.87. When the temperature reached about 50° C., 1.68 ml of dibutyl tin dilaurate was added, and the mass was allowed to exotherm. The mass was heated at 100 C for about one hour to complete formation of the polymer. The polymers can be used in shaving lotions, creams and foams, moisturizing lotions and creams, facial creams, animal grooming products, facial and body hair removal products, and antiperspirants, and in coatings of metals, plastics, elastomers, including polyolefins, polystyrene, silicone rubber, polyurethane, steel, brass, bronze to enhance slip, adhesion and biocompatibility. The coatings are useful in industrial applications and in medical devices.

EXAMPLE 37

Polyoxyethylene diol having an average molecular weight of 8000 was heated under vacuum to reduce the water level, and 699 parts of the dried diol was added to 50 parts of polyoxyethylene diol having a number average molecular weight of 1450, 47 parts of polyoxypropylene diol having a number average molecular weight of 425, and 18 parts of dimethylol propionic acid, and sufficient water to bring the total to 0.31 part. The mixture was heated with stirring until a homogenous melt was obtained. Then, 94 parts of methylene bis-cyclohexyl-4-4'-diisocyanate were added. The NCO/OH ratio was about 0.92. When the temperature reached about 50° C., 1.68 ml of dibutyl tin dilaurate was added, and the mass was allowed to exotherm. The mass was heated at 100 C for about one hour to complete formation of the polymer. The polymers can be used in shaving lotions, creams and foams, moisturizing lotions and creams, facial creams, animal grooming products, facial and body hair removal products, and antiperspirants, and in coatings of metals, plastics, elastomers, including polyolefins, polystyrene, silicone rubber, polyurethane, steel, brass, bronze to enhance slip, adhesion and biocompatibility. The coatings are useful in industrial applications and in medical devices.

EXAMPLE 38

Polyoxyethylene diol having an average molecular weight of 8000 was heated under vacuum to reduce the water level, and 291 parts of the dried diol was added to 15 parts of polyoxyethylene diol having a number average molecular weight of 1450, 34 parts of polyoxypropylene diol having a number average molecular weight of 425, 9.5 parts of dipropylene glycol, and 27 parts of dimethylol propionic acid, and sufficient water to bring the total to 0.141 part. The mixture was heated with stirring until a homogenous melt was obtained. Then, 92 parts of methylene bis-cyclohexyl-4-4'-diisocyanate were added. The NCO/OH ratio was about 0.85. When the temperature reached about 50° C., 0.68 ml of dibutyl tin dilaurate was added, and the mass was allowed to exotherm. The mass was heated at 100 C for about one hour to complete formation of the polymer. The polymers can be used in animal grooming products, facial and body hair removal products, and antiperspirants, and in coatings of metals, plastics, elastomers, including polyolefins, polystyrene, silicone rubber, polyurethane, steel, brass, bronze to enhance slip, adhesion and biocompatibility. The coatings are useful in industrial applications and in medical devices.

The following tables summarize the constituents used in forming the polymer and properties of particular examples related to the first asepct of the present invention. The following tables summarize the constituents used in forming the polymer and properties of particular examples related to the first aspect of the present invention.

TABLE I

| Ex. No. | C8000 | DEG | DW | DMPA | WAT | R | Visc 4% THF/ eth cps |
|---|---|---|---|---|---|---|---|
| 12 | * | * | 39.1 | 8.5 | 0.065 | 0.93 | |
| 15 | | * | 45.2 | 4.1 | 0.33 | 0.98 | 15 |
| 16 | 53.8 | 2.32 | * | 3.6 | 0.018 | 0.92 | |
| 17 | * | | * | 43.8 | 2.03 | 0355 | 15 |

| | TR2000 | PPG1025 | C1450 | C1000 | C600 | C400 | EG |
|---|---|---|---|---|---|---|---|
| 12 | | | 48.7 | | | | 3.65 |
| 15 | 16.8 | 4.6 | 10 | 6.9 | 4.13 | 2.8 | 5.3 |
| 16 | | | | | | | 2.32 |
| 17 | 17.9 | 4.9 | 10.7 | 7.4 | 4.4 | 2.9 | 5.66 |

With 5% water added to Examples 14 and 16, the viscosity increased to 6120 cps.
*additional components The viscosity was measured at a 4% concentration in 75/25 tetrahydrofuran and water.

Tables 2A and 2B summarize the constituents used in forming the polymer and properties of particular examples related to the second aspect of the invention.

TABLE 2A

| Table D | Examples for Patent Application | | | | | | Visc. 5% eth/ wa |
|---|---|---|---|---|---|---|---|
| Ex. No. | C8000 | DEG | DW | DMPA | WAT | R | cps |
| 19 | 82.7 | 2.31 | 12.7 | 2 | 0.26 | 0.75 | 11 |
| 20 | 80.3 | 2.25 | 15.2 | 2 | 0.36 | 0.85 | 16 |
| 25 | 74.5 | 2.08 | 17 | 6 | 0.36 | 0.65 | 7.5 |
| 26 | 82.7 | 2.31 | 12.8 | 2 | 0.16 | 0.85 | 11.5 |

TABLE 2B

| | | | | Set Retention | |
|---|---|---|---|---|---|
| | Crust | Feel | Flake | 30 min | 60 min |
| 19 | 4.2 | 4.8 | 4.2 | 86 | |
| 20 | 8.3 | 9.6 | 8.4 | 94 | |

TABLE 2B-continued

| | | | | Set Retention | |
|---|---|---|---|---|---|
| | Crust | Feel | Flake | 30 min | 60 min |
| 25 | 4.5 | 4.5 | 1.8 | 85 | |
| 26 | 4.9 | 6.7 | 7 | 90 | 95 |

In contrast to prior art, gels made without carboxylic acids may be tough and highly absorptive, but, due to the lack of the alkanoic acids, do not possess the same adhesive qualities and washability as the gels of this invention.

While the invention has been described with reference to the preferred embodiment, this description is not intended to be limiting. It will be appreciated by those of ordinary skill in the art that modifications may be made without departing from the spirit and scope of the invention.

We claim:

1. A hydrophilic polyether polyurethane polymer of improved strength, absorption and integrity comprising the reaction product of a mixture of:

a long chain polyoxyalkylene diol, said polyoxyalkylene diol comprising one or more of a higher molecular weight polyoxyethylene diol having a number average molecular weight of about 6,000 to about 10,000 in an amount by weight in the reaction mixture of least about 55%, a polyoxypropylene having a number average molecular weight of about 400 to about 3,500 or lower molecular weight polyoxyethylene diol having a number average molecular weight of about 600 to about 2,000;

a glycol selected from the group consisting of ethylene glycol, propylene glycol, 2-ethyl-1,3-hexanediol, tripropylene glycol, triethylene glycol, 2,-4-pentanediol, 2-methyl-1,3-propanediol, cyclohexanediol, cyclohexanedimethanol, 2-methyl-1,3-pentanediol, dipropylene glycol, diethylene glycol in an amount by weight of the reaction mixture of about 1.0% to about 5.0%;

an organic diisocyanate;

a 2,2-di-(hydroxymethyl) alkanoic acid in the amount comprising about 0.5% to about 2.7% by weight of the reaction mixture, the alkanoic acid is dimethylolpropionic acid; and water in the amount comprising from about 0.10% to about 0.30% by weight of the reaction mixture, wherein the ratio of NCO to OH of the long chain polyoxyalkylene diol, the alkanoic acid, water and glycol being from about 0.75 to about 0.95, the weight average molecular weight of the reaction product is about 25,000 to about 55,000 and said polymer is soluble in a basic water solution.

2. The polymer of claim 1 wherein the amount by weight of said higher molecular weight polyoxyethylene diol in the reaction mixture is at least 75%.

3. The polymer of claim 1 where the polymer has a weight average molecular weight in the range of about 25,000 to about 55,000.

4. A solution formed of the polymer of claim 1.

5. A lotion formed of the polymer of claim 1.

6. A cream formed of the polymer of claim 1.

7. A coating of improved slip formed of the polymer of claim 1.

8. The coating of claim 7 wherein the coating is applied in shaving preparations.

9. A coating of improved absorption formed of the polymer of claim 1.

10. A hydrophilic polyether polyurethane polymer of improved strength and integrity comprising the reaction product of a mixture of:
- a long chain polyoxyalkylene diol, said polyoxyalkylene diol comprising one or more of a higher molecular weight polyoxyethylene diol having a number average molecular weight of about 4000 to about 15000 in an amount of at least about 40% by weight of the reaction mixture, a lower molecular weight polyoxypropylene diol having a number average molecular weight of about 400 to about 3,000 in an amount of about 0.2% to about 20% by weight of the reaction mixture or a lower molecular weight polyoxyethylene diol having a number average molecular weight of about 600 to about 2,000 in an amount of about 2% to about 30% by weight of the reaction mixture;
- a glycol selected from the group consisting of ethylene glycol, propylene glycol, 2-ethyl-1,3-hexanediol, tripropylene glycol, triethylene glycol, 2,-4-pentanediol, 2-methyl-1,3-propanediol, cyclohexanediol, cyclohexanedimethanol, 2-methyl-1,3-pentanediol, dipropylene glycol, diethylene glycol, in an amount by weight of the reaction mixture of about 1.0% to about 5.0%,
- an organic diisocyanate;
- a 2,2-di-(hydroxymethyl) alkanoic acid in the amount comprising 0.30% to about 2.5% by weight of the reaction mixture, the alkanoic acid is dimethylolpropionic acid; and
- water in the amount comprising from about 0.02% to about 0.25% by weight of the reaction mixture,
- wherein the ratio of NCO to OH of the long chain polyoxyalkylene, diol, water, alkanoic acid and the alkylene glycol being from about 0.88 to about 0.98.

11. The polymer of claim 10 wherein the amount by weight of said polyoxyethylene diol having a number average molecular weight of about 4000 to about 15,000 in the reaction mixture is at least about 65%.

12. The polymer of claim 10 wherein the amount of polyoxypropylene diol is in the range of about 0.3% to about 7.0% by weight of the reaction mixture.

13. A wound dressing formed of the polymer of claim 10.

14. A high slip coating formed of the polymer of claim 10.

15. The coating of claim 14 wherein the coating is applied to a plastic, razor, razor strip, catheter, guidewire or cloth.

16. An absorptive coating formed of the polymer in claim 10.

17. A lotion formed of the polymer in claim 10.

18. A cream formed of the polymer of claim 10.

19. A depilatory formed of the polymer of claim 10.

20. An animal grooming product formed of the polymer of claim 10.

21. An antiperspirant formed of the polymer of claim 10.

22. A gel formed of the polymer of claim 10.

23. A foam formed of the polymer of claim 10.

* * * * *